US00PP37249P2

(12) United States Plant Patent
Walters

(10) Patent No.: US PP37,249 P2
(45) Date of Patent: Feb. 3, 2026

(54) ***LOBELIA* PLANT NAMED 'Neon Nights'**

(50) Latin Name: ***Lobelia* x *speciosa* (Sweet)**
Varietal Denomination: Neon Nights

(71) Applicant: Chad M. Walters, Hudsonville, MI (US)

(72) Inventor: Chad M. Walters, Hudsonville, MI (US)

( * ) Notice: Subject to any disclaimer, the term of this patent is extended or adjusted under 35 U.S.C. 154(b) by 0 days.

(21) Appl. No.: 18/831,749

(22) Filed: Aug. 1, 2025

(51) Int. Cl.
*A01H 5/02* (2018.01)
*A01H 5/12* (2018.01)
*A01H 6/26* (2018.01)

(52) U.S. Cl.
USPC ..... Plt./421
CPC ..... *A01H 6/268* (2018.05); *A01H 5/02* (2013.01); *A01H 5/12* (2013.01)

(58) Field of Classification Search
USPC ..... Plt./451
See application file for complete search history.

*Primary Examiner* — Susan Mccormick Ewoldt

(57) ABSTRACT

The new and distinct *Lobelia* plant named 'Neon Nights' with strongly upright habit of dark purple branched stems and dark greyed-purple oblanceolate foliage supporting numerous hot-fuchsia-colored flowers over an eight-week period beginning in late June.
'Starship™ Rose'='PAS1302714'
Starship™ Scarlet Bronze Leaf='PAS1302716'

2 Drawing Sheets

Botanical classification: *Lobelia* x *speciosa* (Sweet).
Variety denomination: 'Neon Nights'.

STATEMENT REGARDING PRIOR DISCLOSURES UNDER 37 CFR 1.77(B)(6)

The first offer for sale was made by Walters Gardens, Inc. to Prides Corner on Jul. 24, 2025. Walters Gardens, Inc. obtained the new plant and all information relating thereto, from the inventor. No plants of *Lobelia* 'Neon Nights' have been sold, in this country or anywhere in the world, nor has any disclosure of the new plant been made, more than one year prior the filing date of this application, and such sale or disclosure within one year was either derived directly or indirectly from the inventor and is therefore a 35 U.S.C 102(b) exception.

BACKGROUND OF THE INVENTION

The present invention relates to the new and distinct clustered bellflower herein also referred to as *Lobelia* 'Neon Nights', by the cultivar name, 'Neon Nights', or as the "new plant." The new plant was discovered by the inventor, Chad M. Walters, in spring 2022 in a seed batch of *Lobelia* 'PAS1302716' (not patented) at a perennial nursery in Hudsonville. During trials the plant was named Legacy Hot Fuchsia.

Asexual propagation at the same nursery in Hudsonville, MI, USA by division since 2022 and later by basal cuttings and shoot tip tissue culture have all shown 'Neon Nights' to be stable and reproduce true to type in successive generations.

SUMMARY OF THE PLANT

*Lobelia* 'Neon Nights' has not been observed in all possible environmental conditions. The phenotype may vary slightly with changes in environments such as light intensity, fertility, water availability, etc. without, however, any variation in genotype.

*Lobelia* 'Neon Nights' is distinct from all cultivars known to the inventor in the following traits:

1. Oblanceolate, serrulate, dark-green foliage with heavy blush to solid dark purple;
2. Strongly upright, dark purple stems are branched and full of hot-fuchsia-colored flowers along stem and clustered at ends;
3. Long flowering period, without the need for vernalization, beginning in late-June and continuing for about eight weeks.

Plants of *Lobelia* 'Neon Nights' are most similar to 'Scarlet Princess' U.S. Plant Pat. No. 24,944, 'Crimson Princess' U.S. Plant Pat. No. 24,945, 'Rose Princess' U.S. Plant Pat. No. 24,930, and 'PAS1302716' and 'PAS1302714' (not patented).

'Scarlet Princess' is smaller in habit with fewer and smaller flowers that are more reddish scarlet. 'Crimson Princess' is smaller in habit and produces fewer and smaller flowers that are dark purplish-red. 'Rose Princess' is smaller in habit in both height and width and the flowers are a lighter purplish-red. 'PAS1302714' has flowers that are lighter reddish-colored and lacks the greyed-purple coloring on the foliage.

The parent, 'PAS1302716', has a flower color that is more scarlet red.

BRIEF DESCRIPTION OF THE DRAWINGS

The color drawings illustrate the overall characteristics of *Lobelia* 'Neon Nights' as a one-year-old plant. The colors are as true as reasonably possible given the technology available. The color values may vary slightly depending on light intensity and quality.

DETAILED BOTANICAL DESCRIPTION

Figure 1:
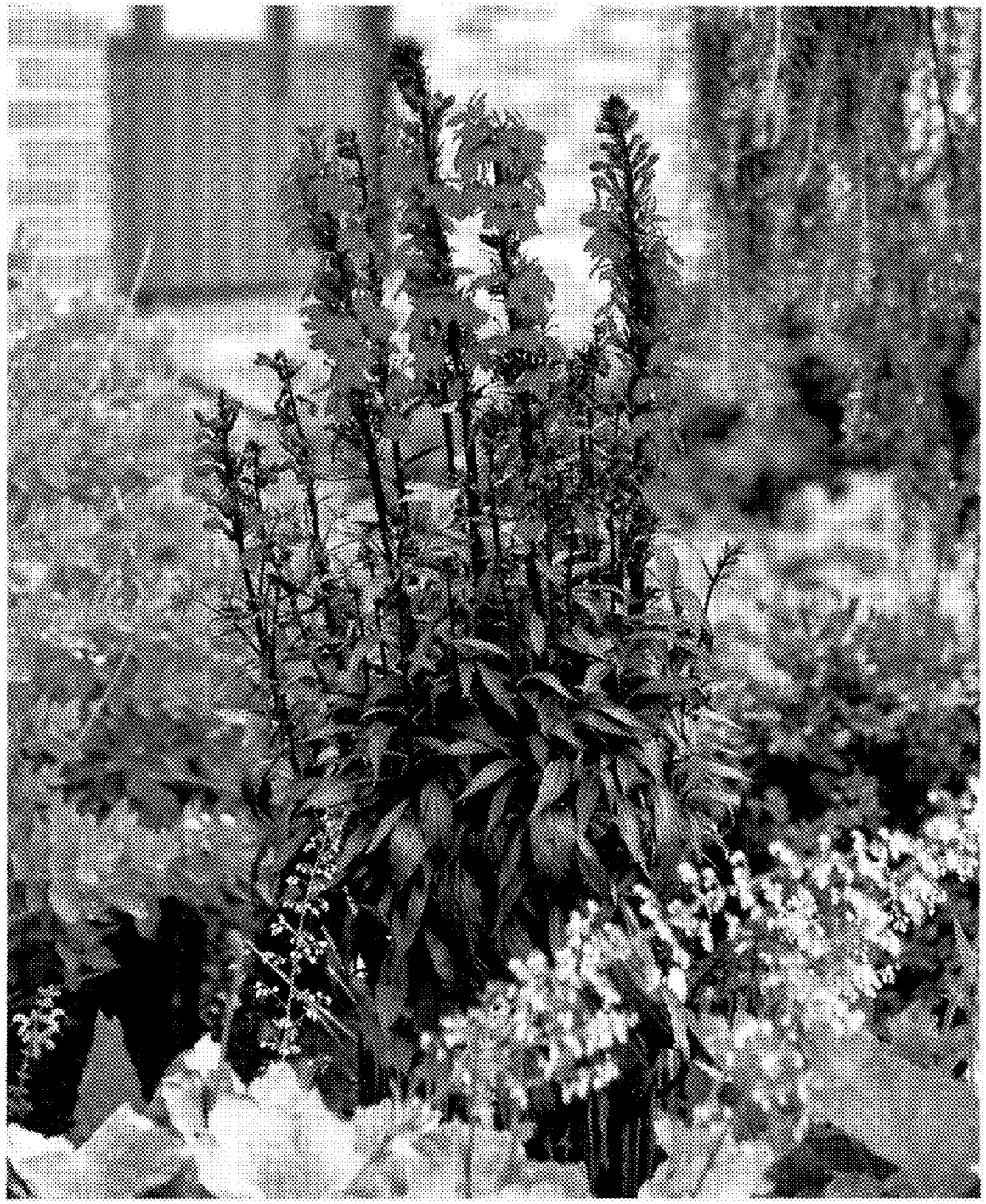
FIG. 1 shows the new plant in a landscape environment in peak flower.
Figure 2:
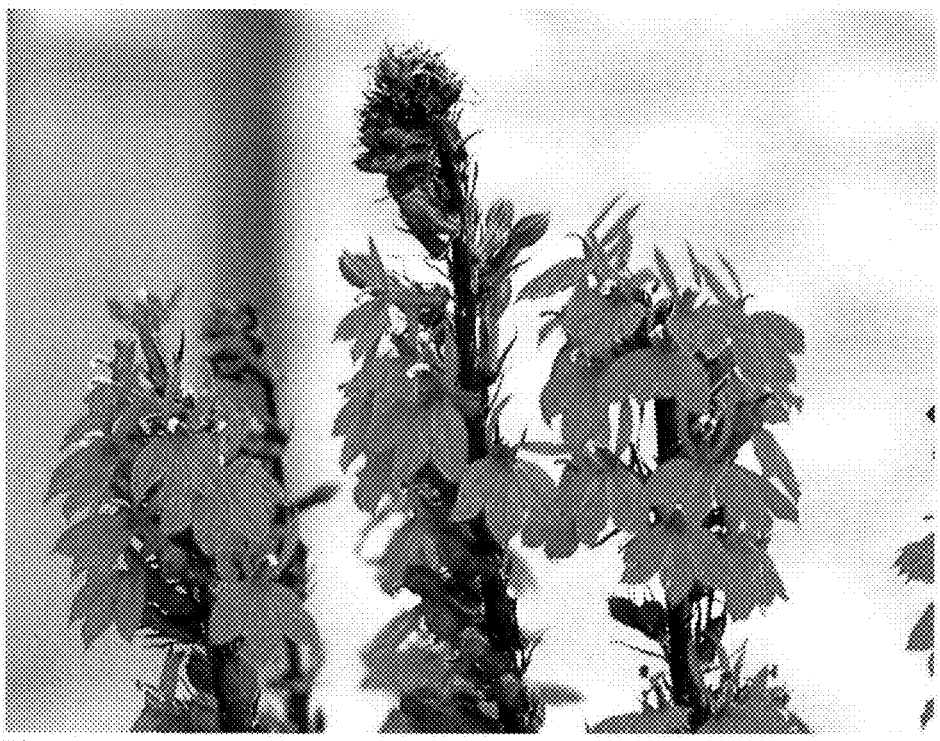
FIG. 2 shows a close-up of the flowers of the new plant.
Figure 3:
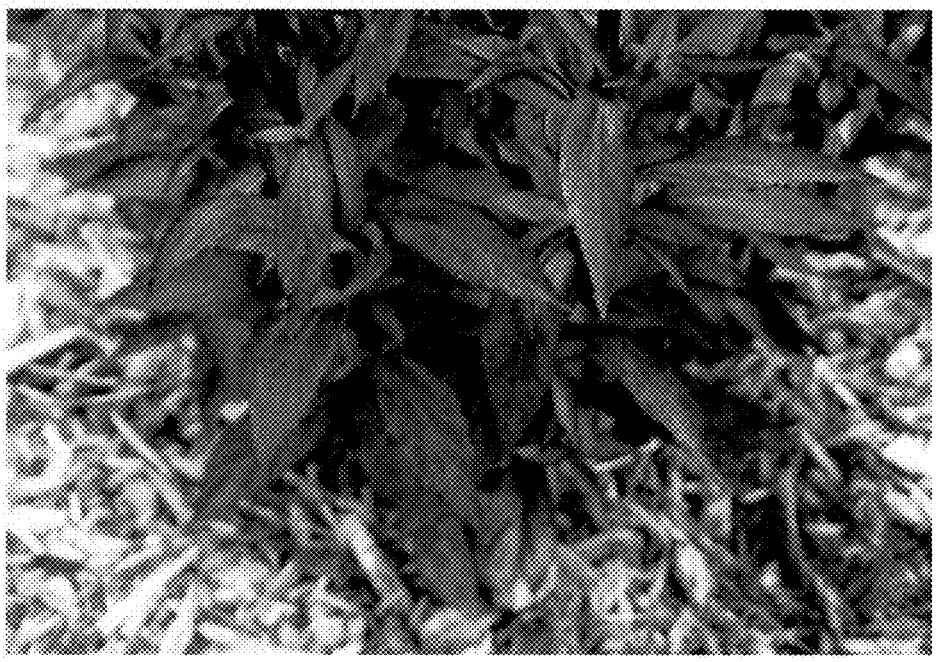
FIG. 3 shows a close-up of the young expanding and maturer foliage.

The following description is based on a two-year-old plant growing in a full-sun display garden in Zeeland, MI, USA. Environmental conditions for the growing season daytime temperatures range between 12° C. to 35° C., and night temperatures range between 6° C. to 24° C. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: The parent is 'PAS1302716';

Asexual propagation: Cuttings, about 14 days to initiate roots; time to finish in a 3.8-liter container about 18 weeks, flowering without a vernalization period;

Roots: Thin, fibrous, and highly branching; color between RHS 158D and RHS NN155B;

Plant habit: Up-right, herbaceous, winter-hardy, perennial mound; with branched flower stems up to 90 cm tall; average about 82 cm tall and about 50 cm across;

Leaves: Oblanceolate; simple; sessile; alternate to dextrose; adaxial glabrous and abaxial micro-puberulent; adaxial and abaxial matte; acute apex; attenuate base; margin serrulate with teeth about 2 mm apart, 0.7 mm long and 0.7 mm wide;

Leaf size: To 10 cm long and 3 cm wide, average about 9 cm long and 2.4 cm wide;

Leaf color: Young expanding leaves adaxial between RHS 146B and RHS 143B with margins or teeth nearest RHS 187A, young expanding abaxial between RHS 146C and RHS 144A with margins or teeth nearest RHS 187A; mature leaves adaxial between RHS 187A and RHS N187A with an undertone of nearest RHS NN137B where direct sun exposure is shaded, abaxial nearest RHS 187A with variable blotches of RHS NN37C and RHS 146B;

Veins: Pinnate; glabrous adaxial and abaxial;

Vein color: Adaxial variable between RHS 187A and RHS N187A in high sun exposure and nearest RHS NN137B where direct sun exposure is shaded; abaxial variable, nearest RHS 146B, nearest RHS 187B and between RHS 148B and RHS 185D;

Petiole: Sessile;

Inflorescence: Panicle; aspect erect, upright; lightly branched; flowering in the upper 40 cm and 9 cm wide; about 60 flowers per main panicle, 24 flowers per branch;

Flower: Single; perfect; complete; zygomorphic; protandrous; on terminal panicles; about 35 mm deep and about 35 mm across at widest point; narrowing forming a corolla tube about 20 mm long with a dorsal split between the bend and base; to about 5 mm diameter in middle and swelling to about 6 mm diameter near base; aspect upright;

Flower fragrance: Not detected;

Flowering period: Beginning late June for about 8 weeks; up to 60 flowers per main panicle, 24 per branch, and 120 per peduncle;

Flower longevity: 5 to 7 days;

Flower buds one day prior to opening: Clavate to pyriform; rounded apex and rounded base; about 30 mm long and 8 mm diameter distally and 5 mm diameter near base; moderately carinate;

Flower bud color: Nearest RHS 61A with carinae nearest RHS 187A;

Petals: Five; three oblanceolate lower petals and two linear upper petals;

*Lower petals.*—3 lobed; lobes oblanceolate; with apiculate apices; entire margin; carinate along lobe adaxial fusion lines; glabrous adaxial and abaxial blades, micro-puberulent on adaxial and abaxial veins in the corolla tube portion; connate in the proximal 12 mm and free in the distal 10 mm; to 22 mm long from corolla tube to apex and 11 mm wide at fusion; reflexed to about 90° from corolla tube in the distal one-half; to about 22 mm long from bend to apex, 20 mm long from bend to base, and to about 35 mm across.

*Upper petals.*—2 lobed; linear; free and not connate; divergent to 38 mm across at apices; apex acute to apiculate; base truncate; margin entire; glabrous adaxial and abaxial except abaxial basal 3 to 4 mm micro-puberulent; to about 38 mm long and 4 mm wide near middle.

Petal color: Upper and lower adaxial blades nearer RHS 61B than RHS 61A with midribs and carina nearest RHS N186D; upper and lower adaxial corolla tube basal 3 mm center of petals nearest RHS N155B and distal portion and edge of fused petals; distal corolla tube between RHS 60B and RHS 60C with carina and midribs nearest RHS N186D; upper and lower abaxial blades between RHS 61B and RHS 60C with midribs and carina nearest RHS N186D; upper and lower abaxial corolla tube nearest RHS 60B with midribs and carina nearest RHS N168D;

Androecium: Five;

*Filament.*—Applanate; glabrous adaxial and micro-puberulent abaxial; connate in the distal 21 mm and about 1.5 to 2.5 mm across; to about 25 mm long; color adaxial distil one-half between RHS 63B and RHS 61B and proximal one-half transitioning to between RHS NN155C and RHS N155B; abaxial distal three-quarters nearer RHS 61B than RHS 61A and transitioning to between RHS NN155C and RHS N155B with a basal midrib of nearest RHS 63D.

*Anther.*—Oblong; connate into cylinder; penicillate; with a basifixed; longitudinal; about 5 mm long and 2 mm diameter; color adaxial between RHS N200B and RHS N200A, abaxial nearest RHS 201A.

*Pollen.*—Abundant; color nearest RHS 153A.

Gynoecium: Single; half-inferior; about 32 mm long;

*Style.*—Cylindrical; about 28 mm long and 1 mm diameter; color proximally nearest RHS 187D and distally nearest RHS 187B.

*Stigma.*—Penicillate; to about 1 mm long and 2 mm diameter; color nearest RHS N199A.

*Ovary.*—Spherical to ellipsoidal; acute apex; rounded base; about 5 mm tall and 4 mm diameter at middle; nearest RHS 145A with moderate blush nearest RHS 187C.

Calyx: Campanulate; apices divergent; to about 11 mm long and 16 mm wide at apex;

Sepals: Five; linear; glabrous and slightly lustrous adaxial and abaxial; narrowly acute apex; fused in the basal 2 mm forming hypanthium; apices divergent; margin entire;

glabrous adaxial and abaxial; about 20 mm long above hypanthium, about 3.5 mm wide above fusion;

Sepal color: Adaxial and abaxial nearest RHS N186B with high sunlight exposure and nearest RHS 146A where protected from high sunlight;

Inflorescence: Panicle with flowers arranged in clusters at whorls; flowering in upper 40 cm and 9 cm wide;

Stem: To about 25 per plant; cylindrical, carinate to shallowly fluted; glabrous; slightly lustrous; with about 16 nodes below flowering branches; to about 37 cm long below flower and 8 mm diameter at base; average internode spacing about 2.3 cm below flowers;

Stem color: Color: nearest RHS N186C with an undertone of RHS 146A in regions shaded from direct sunlight;

Peduncle: About 25 per plant; carinate; upright attitude; strong; stiff; to about 6 mm diameter below individual flowers; about fifteen branching nodes, average internode spacing about 2.3 cm below flowers; branches to about 19 cm long and 4 mm diameter at base;

Peduncle branches: Moderately-branched with about four branches; to about 43 cm long and 4 mm diameter at base; branch angle to about 75° above horizontal;

Peduncle and branch color: Between RHS N1186B and RHS N186C;

Pedicel: Cylindrical; puberulent; stiff; strong; about 10 mm long and 2 mm diameter;

Pedicel color: Between RHS 145A and RHS 146D;

Seed: Slightly flattened ellipsoidal; rounded apex and base; surface glabrous; about 1 mm long and 0.5 mm across center;

Seed color: Nearest RHS 20A;

*Lobelia* 'Neon Nights' is tolerant of winter temperatures from USDA hardiness at least to zones 6 to 10. The new plant grows best with plenty of moisture and flowers without requiring a vernalization period. The new plant has not been observed to be more susceptible or more resistant to diseases and pest that are common to other *Lobelia* cultivars.

I claim:

1. The new and distinct cultivar of *Lobelia* plant named 'Neon Nights' as herein described and illustrated.

* * * * *